(12) United States Patent
Lee et al.

(10) Patent No.: US 11,124,548 B2
(45) Date of Patent: Sep. 21, 2021

(54) METHOD FOR EXPRESSING AND PURIFYING SOLUBLE PROTEIN OF CRM197

(71) Applicant: FORBIOKOREA CO., LTD., Seoul (KR)

(72) Inventors: Hyeon Cheol Lee, Seongnam-si (KR); Bong Seong Koo, Seoul (KR); Hyoung Jong Seo, Seoul (KR); Jin Sook Kim, Gwangmyeong-si (KR); Ah Reum Park, Pyeongtaek-si (KR); Seung Won Jang, Uijeongbu-si (KR)

(73) Assignee: FORBIOKOREA CO., LTD., Seoul (KR)

( * ) Notice: Subject to any disclaimer, the term of this patent is extended or adjusted under 35 U.S.C. 154(b) by 140 days.

(21) Appl. No.: 16/479,784

(22) PCT Filed: Jan. 30, 2018

(86) PCT No.: PCT/KR2018/001293
§ 371 (c)(1),
(2) Date: Jul. 22, 2019

(87) PCT Pub. No.: WO2018/143648
PCT Pub. Date: Aug. 9, 2018

(65) Prior Publication Data
US 2019/0352344 A1    Nov. 21, 2019

(30) Foreign Application Priority Data
Feb. 1, 2017   (KR) .................. 10-2017-0014446

(51) Int. Cl.
*C07K 14/34* (2006.01)
*C07K 1/22* (2006.01)

(52) U.S. Cl.
CPC ............ *C07K 14/34* (2013.01); *C07K 1/22* (2013.01); *C07K 2319/21* (2013.01); *C07K 2319/24* (2013.01); *C07K 2319/95* (2013.01)

(58) Field of Classification Search
None
See application file for complete search history.

(56) References Cited

U.S. PATENT DOCUMENTS

| | | |
|---|---|---|
| 5,614,382 A | 3/1997 | Metcalf |
| 6,071,734 A | 6/2000 | Yoon et al. |
| 8,530,171 B2 | 9/2013 | Retallack et al. |
| 2015/0376245 A1 | 12/2015 | Ihssen et al. |
| 2016/0333057 A1 | 11/2016 | Oganesyan et al. |

FOREIGN PATENT DOCUMENTS

| | | |
|---|---|---|
| EP | 2 445 930 A1 | 5/2012 |
| KR | 10-2012-0095837 A | 8/2012 |
| KR | 10-2016-0077750 A | 7/2016 |
| KR | 10-2016-0128362 A | 11/2016 |
| WO | WO 2010/150230 A1 | 12/2010 |

OTHER PUBLICATIONS

Sun et al (Enhancing the solubility of recombinant proteins in *Escherichia coli* by using hexahistidine-tagged maltose-binding protein as a fusion partner. Methods Mol Biol. 2011;705:259-74).*
Mamat et al (Microbial Cell Factories, 14:57, 2015).*
International Search Report for PCT/KR2018/001293 dated Feb. 15, 2019 from Korean Intellectual Property Office.

* cited by examiner

*Primary Examiner* — Brian Gangle
(74) *Attorney, Agent, or Firm* — Paratus Law Group, PLLC

(57) ABSTRACT

Disclosed is a method for producing soluble CRM197 protein at high yield by overexpressing the protein in the cytoplasm of *E. coli*. The method includes a step of culturing recombinant *E. coli* harboring an expression plasmid carrying a gene sequence coding for a recombinant CRM197 protein under a condition suitable for expression of the recombinant CRM197 protein which has a histidine-tag attached to the C-terminus of CRM197 and a maltose-binding protein (MBP) attached to the N-terminus of CRM197. The method further includes a step of purifying after the culturing, wherein the step of purifying comprises a step of treating with tobacco etch virus (TEV) protease to remove the maltose-binding protein and a step of removing the histidine-tag via histidine-tag affinity chromatography.

4 Claims, 8 Drawing Sheets
Specification includes a Sequence Listing.

FIG. 2

GADDVVDSSK SFVMENFSSY HGTKPGYVDS IQKGIQKPKS GTQGNYDDDW KEFYSTDNKY
DAAGYSVDNE NPLSGKAGGV VKVTYPGLTK VLALKVDNAE TIKKELGLSL TEPLMEQVGT
EEFIKRFGDG ASRVVLSLPF AEGSSSVEYI NNWEQAKALS VELEINFETR GKRGQDAMYE
YMAQACAGNR VRRSVGSSLS CINLDWDVIR DKTKTKIESL KEHGPIKNKM SESPNKTVSE
EKAKQYLEEF HQTALEHPEL SELKTVTGTN PVFAGANYAA WAVNVAQVID SETADNLEKT
TAALSILPGI GSVMGIADGA VHHNTEEIVA QSIALSSLMV AQAIPLVGEL VDIGFAAYNF
VESIINLFQV VHNSYNRPAY SPGHKTQPFL HDGYAVSWNT VEDSIRTGF QGESGHDIKI
TAENTPLPIA GVLLPTIPGK LDVNKSKTHI SVNGRKIRMR CRAIDGDVTF CRPKSPYVG
NGVHANLHVA FHRSSSEKIH SNEISSDSIG VLGYQKTVDH TKVNSKLSLF FEIKSKLAAA
LEHHHHHH (SEE ID NO: 1)

FIG. 5
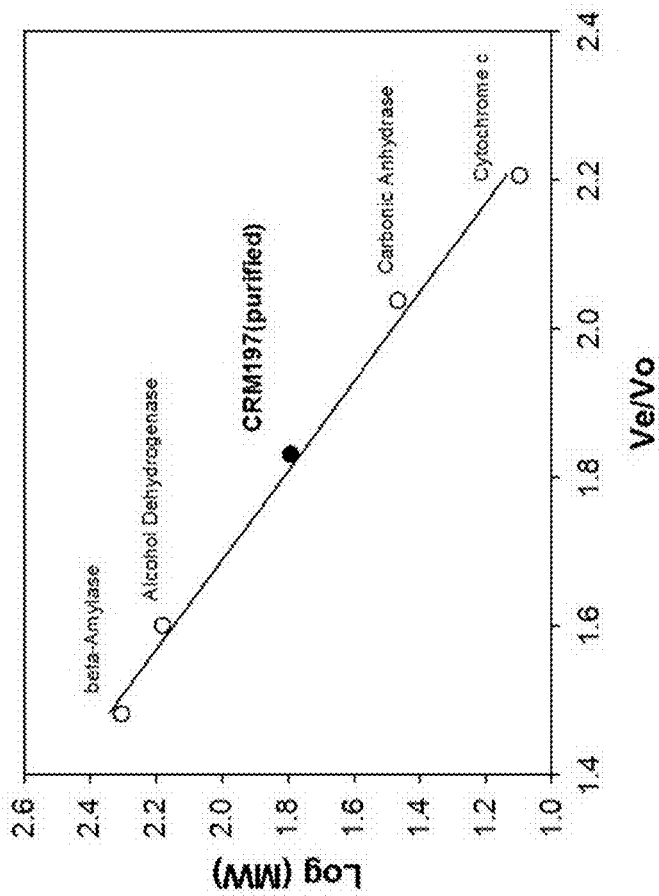
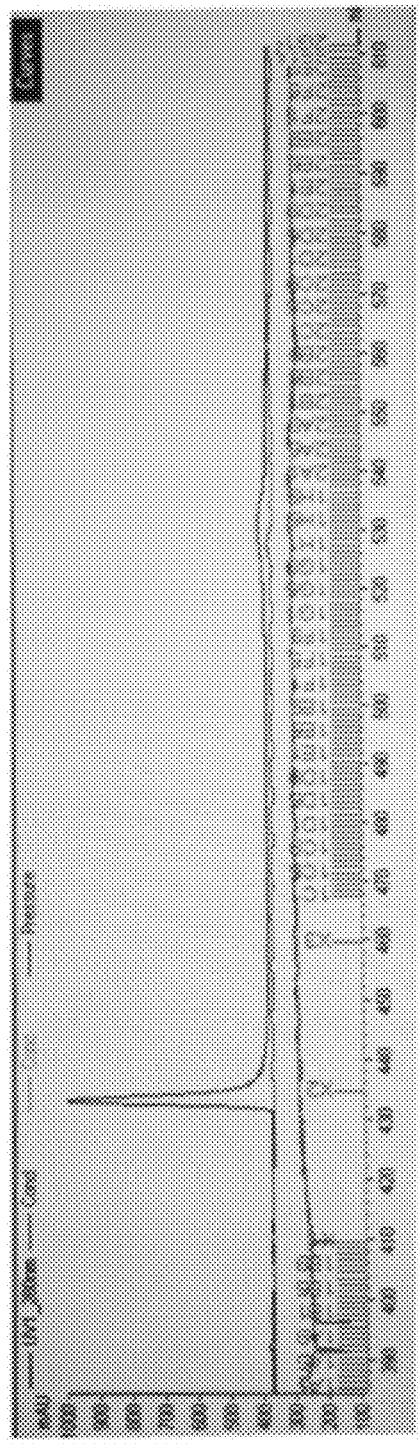

SEQUENCE LISTING

<160> NUMBER OF SEQ ID NOS: 2

<210> SEQ ID NO 1
<211> LENGTH: 548
<212> TYPE: PRT
<213> ORGANISM: Artificial Sequence
<220> FEATURE:
<223> OTHER INFORMATION: Synthetic CRM197 peptide

<400> SEQUENCE: 1

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
```

-continued

```
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser Lys Leu Ala Ala Ala Leu Glu His His
    530                 535                 540

His His His His
545

<210> SEQ ID NO 2
<211> LENGTH: 7
<212> TYPE: PRT
<213> ORGANISM: Artificial Sequence
<220> FEATURE:
<223> OTHER INFORMATION: Linker peptide

<400> SEQUENCE: 2

Lys Leu Ala Ala Ala Leu Glu
1               5
```

METHOD FOR EXPRESSING AND PURIFYING SOLUBLE PROTEIN OF CRM197

CROSS-REFERENCE TO PRIOR APPLICATIONS

This application is a National Stage Patent Application of PCT International Patent Application No. PCT/KR2018/001293 filed on Jan. 30, 2018 under 35 U.S.C. § 371, which claims priority to Korean Patent Application No. 10-2017-0014446 filed on Feb. 1, 2017, which are all hereby incorporated by reference in their entirety.

REFERENCE TO A SEQUENCE LISTING SUBMITTED VIA EFS-WEB

The content of the ASCII text file of the sequence listing named "2021-07-16_659-0020_amended_sequence_listing_CRF", which is 5.31 kb in size, was created on Jul. 16, 2021 and electronically submitted via EFS-Web on Jul. 16, 2021, is incorporated herein by reference in its entirety.

BACKGROUND

The present invention relates to a method for expressing and purifying CRM197 protein, and more particularly, to a method for overexpressing and purifying soluble CRM197 proteins in the cytoplasm of E. coli.

CRM197 is a non-toxic form of diphtheria toxin (DT), which is a proteinaceous exotoxin synthesized and secreted by pathogenic strains of Corynebacterium diphtheriae, and it is a protein of which toxicity is eliminated by reducing the binding ability of NAD, which is an important coenzyme, through one amino acid substitution G52E.

In the administration of vaccines, many antigens are known to have weak immunogenicity in children and the elderly. Therefore, studies have been carried out to supplement vaccines by conjugating to or administering in combination with vaccine adjuvants such as various polysaccharides, proteins, squalene, and the like. Among them, CRM197 has been proven to exert an excellent effect of enhancing immunogenicity, and among other vaccine adjuvants, it has been most widely used as a conjugated form in order to increase efficiencies of currently used vaccines. As a representative example, it has been applied to and used in Pfizer's Prevenar 13 (Pneumococcal polysaccharide conjugate vaccine), which is used as a pneumococcal vaccine and consists of 13 or less capsular polysaccharides.

A production method of CRM197 is a method using strains of Corynebacterium that have been engineered to produce CRM197 from a mutant of conventional Corynebacterium diphtheria, and the method is currently patented with respect to the strain and its production (U.S. Pat. No. 5,614,382). However, due to the problems of productivity and safety, recombinant production methods have been studied. Among them, Pfenex's patented method, a method for producing CRM197 at high level from recombinant strains of Pseudomonas fluorescens is a representative known method (U.S. Pat. No. 8,530,171).

Methods of using Escherichia coli are also currently being studied. As is known, E. coli is a BL1 level organism which is inexpensive to culture and propagate in comparison to any other species and is the strain most commonly studied by researchers. Therefore, production methods of using E. coli may be advantageous compared to the methods described previously. However, to date, there has been no successful production of recombinant CRM197 via the soluble expression thereof in the cytoplasm. Although E. coli is the most advantageous production strain, CRM197 is expressed in the form of insoluble protein in E. coli. Thus, several attempts to overcome the disadvantage have been reported. First, a method of expressing CRM197 as an insoluble protein, and collecting it and refolding it again (Europe Patent Publication No. 2445930) can result in soluble proteins, but the method has limitations in terms of the production yield and economical efficiency. Meanwhile, a method of obtaining soluble proteins by secreting it into the periplasmic space, which is more oxidative than the cytoplasm, using secretion signals of E. coli (US Patent Publication No. 2016/333057) was proposed as a more efficient method than the refolding method. However, this method resulted in the secretion of the proteins into the periplasmic space, which has relatively small production capacity compared to the cytoplasm, and thus, is also considered to be somewhat less productive.

Thus, there is a need for methods to produce CRM197 in E. coli in an efficient and cost-effective manner.

SUMMARY

Accordingly, the present invention is intended to provide a method for producing soluble CRM197 protein at high yield by overexpressing the protein in the cytoplasm of E. coli.

In order to solve the above problem, the present invention provides a method for producing a recombinant CRM197 protein soluble in the cytoplasm, the method comprising a step of culturing recombinant E. coli harboring an expression plasmid carrying a gene sequence coding for a recombinant CRM197 protein under a condition suitable for expression of the recombinant CRM197 protein which has a histidine-tag attached to the C-terminus of CRM197 and a maltose-binding protein (MBP) attached to the N-terminus of CRM197.

Also, the present invention provides the method, wherein the expression plasmid has the genetic map of FIG. 1.

In addition, the present invention provides the method, wherein the E. coli is endotoxin-free E. coli BL21 (DE3).

Furthermore, the present invention provides the method, wherein the recombinant E. coli is BC-mC1h (Accession number: KCCM11958P).

Still further, the present invention provides the method further comprising a step of purifying after the culturing, wherein the step of purifying comprises a step of treating with tobacco etch virus (TEV) protease to remove the maltose-binding protein and a step of removing the histidine-tag via histidine-tag affinity chromatography.

The present invention provides a method for producing a recombinant CRM197 protein soluble in the cytoplasm, the method comprising a step of culturing recombinant E. coli harboring an expression plasmid carrying a gene sequence coding for a recombinant CRM197 protein under a condition suitable for expression of the recombinant CRM197 protein which has a histidine-tag attached to the C-terminus of CRM197 and a maltose-binding protein (MBP) attached to the N-terminus of CRM197.

BRIEF DESCRIPTION OF THE DRAWINGS

FIG. 2 is the amino acid sequence of the active CRM197 having MBP removed in Example 1 of the present invention.

FIG. 5 is a graph showing the result of SEC analysis of the purified CRM197 in Example 4 of the present invention.

DETAILED DESCRIPTION

Figure 1:
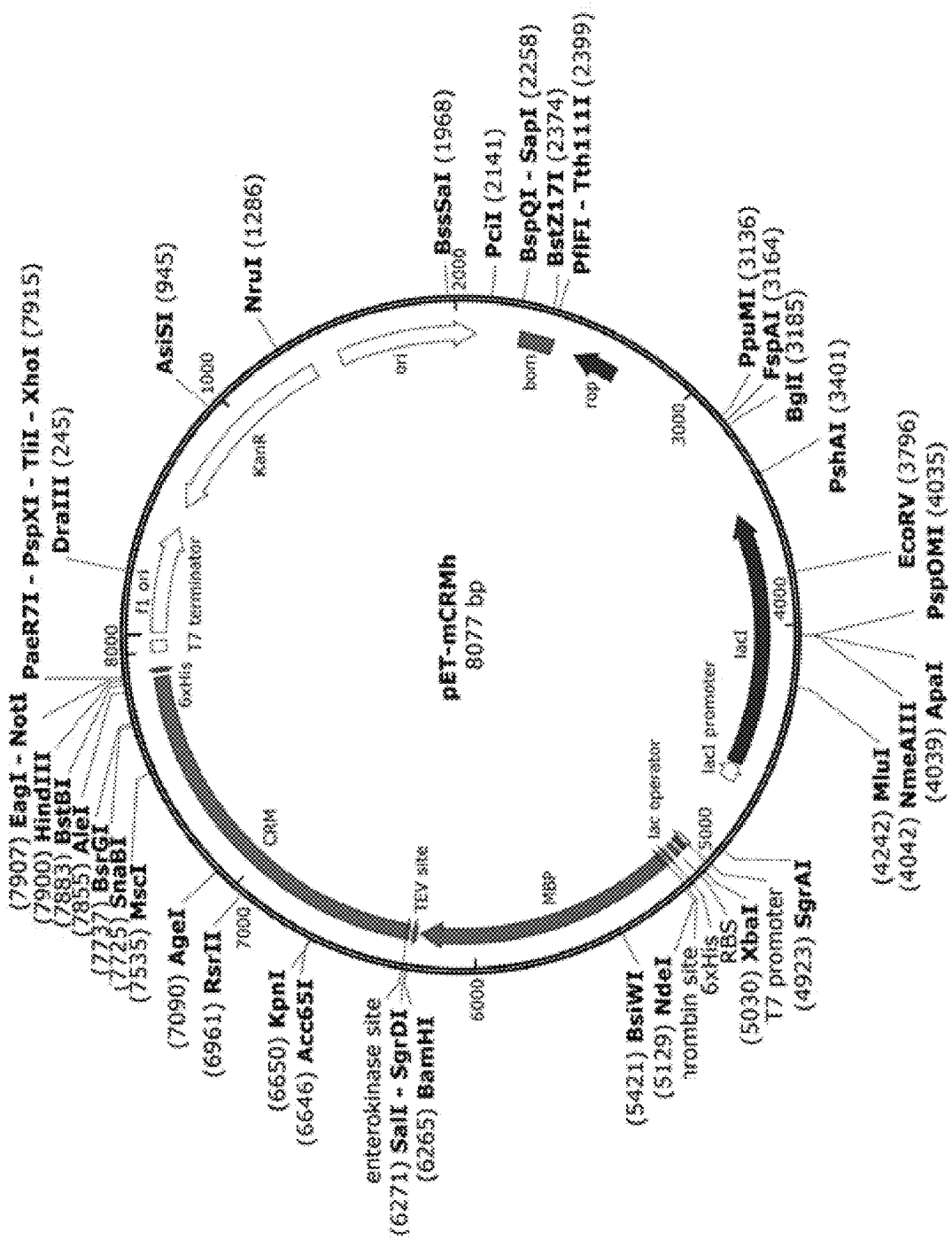
FIG. 1 is the genetic map of an expression plasmid of soluble CRM197.
Figure 3:
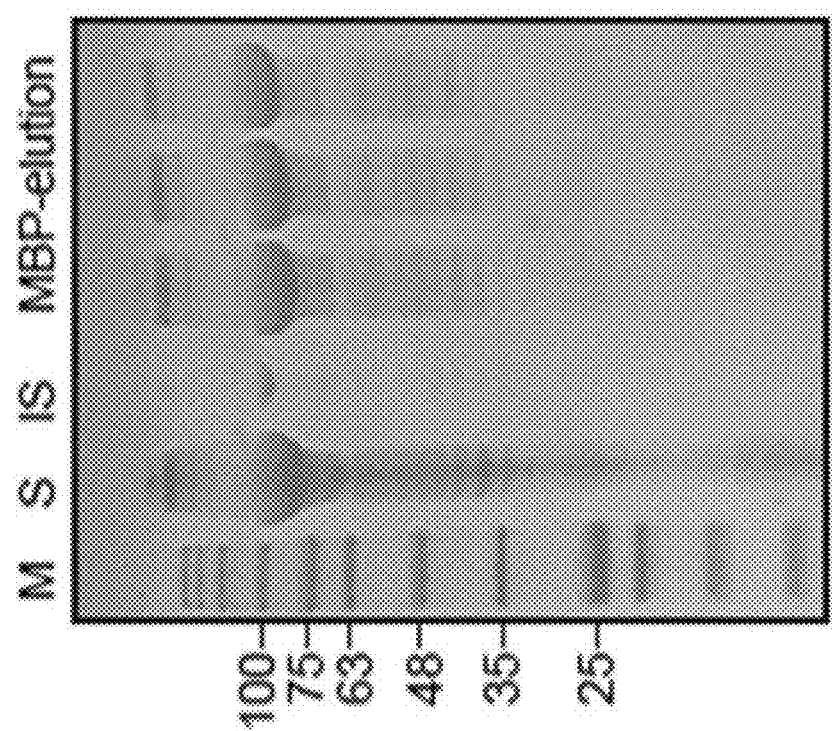
FIG. 3 is a photograph showing the results of the expression of soluble protein of MBP-CRM197 and confirmation of the purified protein by MBP-affinity chromatography in Example 2 of the present invention.
Figure 4:
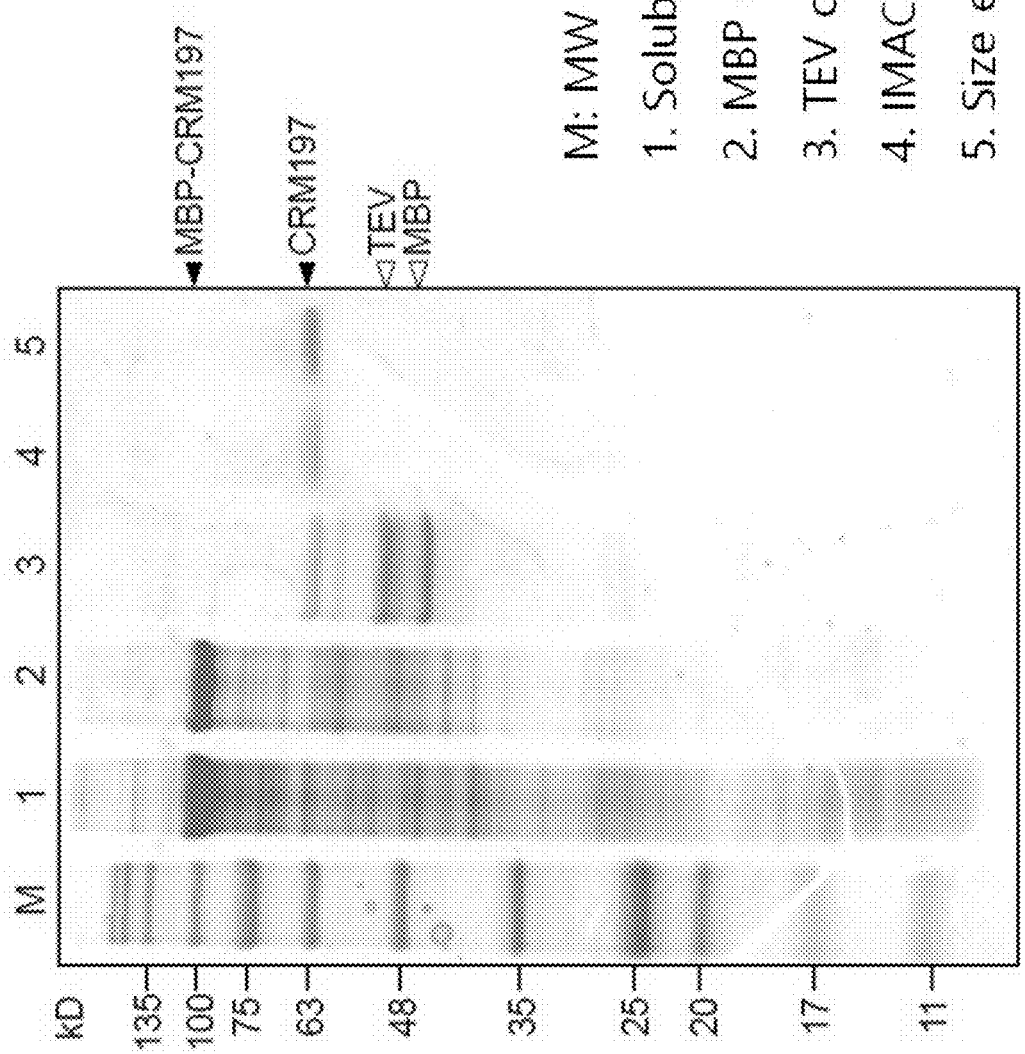
FIG. 4 is a photograph showing the results of SDS-PAGE analysis of each protein from each purification step in Example 3 of the present invention.

Hereinafter, the present invention will be described in more detail by examples. Prior to this, the terms or words used in the description and claims shall not be interpreted as being limited to ordinary or dictionary meanings and the terms or words should be interpreted as meanings and concepts consistent with the technical idea of the present invention, based on the principle that an inventor may properly define the concept of a term to explain his own invention in the best way. Thus, the example described in the present specification is merely nothing but the most preferred embodiment of the present invention and does not represent all the technical ideas of the present invention. Therefore, it should be understood that various equivalents and modifications which may be substituted for those at the time of the present application can be made thereto.

The present invention is directed to cells, compositions and methods for producing recombinant proteins. The present inventors have conducted extensive studies on production methods for overexpressing soluble CRM197 protein in the cytoplasm of E. coli to obtain the protein at high level and have found that the methods could be accomplished by using endotoxin-free E. coli as an acceptor cell to culture recombinant E. coli harboring an expression plasmid comprising a gene sequence coding for a recombinant CRM197 protein, in which a specific tag and a specific protein have been inserted in the CRM197, and purifying the recombinant E. coli in a specific manner, thereby completing the present invention.

Accordingly, the present invention discloses a method for producing a recombinant CRM197 protein being soluble in the cytoplasm, the method comprising a step of culturing recombinant E. coli harboring an expression plasmid carrying a gene sequence coding for a recombinant CRM197 protein under a condition suitable for expression of the recombinant CRM197 protein which has a histidine-tag attached to the C-terminus of CRM197 and a maltose-binding protein (MBP) attached to the N-terminus of CRM197.

Also, the present invention discloses a method for purifying a recombinant CRM protein being soluble in the cytoplasm, the method further comprising a step of purifying after the culturing, wherein the step of purifying comprises a step of treating with tobacco etch virus (TEV) protease to remove the maltose-binding protein and a step of removing the histidine-tag via histidine-tag affinity chromatography.

The technology embodied in the present invention involves overexpressing the CRM197 protein in the soluble protein form in the cytoplasm in endotoxin-free E. coli (BL21 ClearColi) and purifying the same, and is designed to include additional peptide sequences, but for the additional peptide sequences to be removed during purification, thereby producing the overexpressed CRM197 in the cytoplasm in the form of the protein structurally and immunologically same as the native CRM197.

The CRM197 protein produced in the present invention is soluble in the cytoplasm of E. coli, and is not bound as an insoluble inclusion body of the cells.

The present invention involves recombinant E. coli as a preferable expression system for expressing and producing CRM198 proteins, and a preferable expression system is a recombinant cell, of which example includes a cell containing a synthetic CRM197 coding sequence. A preferable acceptor cell is endotoxin-free E. coli (BL21 ClearColi).

According to the present invention, as a method for mass-producing CRM197, the production amount is typically expressed in mg per L of a cell culture. The production amount of the CRM197 protein according to the method of the present invention is, in a flask culture, 180 mg/L or more, preferably 500 mg/L or more, and in a jar fermenter culture, more preferably 3 g/L or more, even more preferably 10 g/L or more.

According to one embodiment of the present invention, the expression plasmid is an expression plasmid carrying a gene sequence coding for a recombinant CRM197 protein which has a histidine-tag attached to the C-terminus of CRM197 and a maltose-binding protein (MBP) attached to the N-terminus of CRM197 and may have the genetic map of FIG. 1. The expression plasmid may be constructed by carrying out codon optimization, for example, to obtain a synthetic CRM197 gene, then adding specific restriction enzyme sequences to both ends of the obtained gene, then cutting the CRM197 gene and the expression plasmid using the corresponding restriction enzymes to insert the CRM197 gene into the corresponding site of the expression plasmid. For the purification of the corresponding protein after the expression, the expression plasmid may be constructed so as to be expressed in a form in which histidine-tag was added to the C-terminus of CRM197. In addition, the final desired expression plasmid may be constructed by, for soluble expression, inserting a gene containing the maltose-binding protein (MBP) and a TEV protease cleavage site into the N-terminus of the CRM197 gene inserted into the expression plasmid, using specific restriction enzymes.

The expression plasmid prepared as described above allows the obtainment of a transformed E. coli strain producing soluble CRM197, through a transformation method of using E. coli having a gene associated with endotoxin removed (BL21 ClearColi) as an acceptor cell.

According to one embodiment of the present invention, a method of purifying CRM197 with high yield is disclosed and the purification method may comprise a step of treating with tobacco etch virus (TEV) protease to remove the maltose-binding protein and a step of removing the histidine-tag via histidine-tag affinity chromatography.

Specifically, in the present invention, the purification may be carried out using multi-step chromatography and each step of the multi-step chromatography may be proceeded in order of MBP affinity chromatography after the separation of soluble CRM197, fusion partner separation via TEV enzyme, His-tag affinity chromatography (immobilized-metal affinity chromatography (IMAC)), and size-exclusion chromatography (SEC).

Hereinafter, the present invention will be described in more detail by examples.

Example 1: Preparation of Expression Plasmid and Recombinant *E. coli* Strain

Codon optimization was carried out for suitable expression of the CTM197 protein derived from *Corynebacterium diphtheriae* in *E. coli* to obtain a synthetic CRM197 gene. BamHI and HindIII restriction enzyme sequences were added to both termini of the obtained gene and then the CRM197 gene and the expression plasmid were cut out using the corresponding restriction enzymes to insert the obtained gene into the corresponding position of the expression plasmid pET21a. Here, for the purification of the corresponding protein following the expression, the gene was prepared to be expressed in a form in which histidine-tag is added to the C-terminus of CRM197 (see FIG. 1). In addition, pET-mCRMh was prepared by, for soluble expression, inserting a gene containing the maltose-binding protein (MBP) and a TEV protease cleavage site into the N-terminus of the CRM197 gene inserted into the expression plasmid, using Nde I and BamHI restriction enzymes. The pET-mCRMh plasmid was transformed into an acceptor cell, that is, *E. coli* having a gene associated with endotoxin removed (BL21 ClearColi), using CaCl2 transformation method to obtain a transformed *E. coli* strain BC-mC1h producing soluble CRM197. Samples of the transformant BC-mC1h were deposited under the Budapest Treaty on the International Recognition of the Deposit of Microorganisms for Patent Purposes at the Korean Culture Center of Microorganisms (KCCM), Yurim B/D, 45 Hongjenae-2ga-gil Seodaemum-gu, Seoul, 120-861, Republic of Korea, on Jan. 3, 2017 and were given accession number: KCCM11958P. The amino acid sequence encoded from the gene sequence is identical to the sequence shown in FIG. 2 (MW 60.94 kD) except for the MBP fusion partner which is removed during purification, and is identical to the known CRM197 sequence except for the C-terminal His-tag for purification and the linker peptide (SEQ ID2: KLAAALE) for efficient purification.

Example 2: Identification of Purified Protein by MBP-Affinity Chromatography

In order to identify a single polypeptide of the expressed soluble protein, the soluble protein expressed in *E. coli* from each purification step was developed by SDS-PAGE. The result is shown in FIG. 3.

Referring to FIG. 3, the molecular weight of MBP-CRM197 was found to be 103 kD in the soluble fraction, and it was found that it was mostly a soluble protein. It was also found that the soluble fraction was separated by MBP affinity chromatography.

Example 3: Purification of CRM197 Protein

In order to determine the average yield according to the purification process, the CRM197 protein was purified by multi-step chromatography with 1 L of a culture medium.

Each step of the multi-step chromatography was proceeded in order of MBP affinity chromatography after the separation of soluble CRM197, fusion partner separation via TEV enzyme, His-tag affinity chromatography (immobilized-metal affinity chromatography (IMAC)), and size-exclusion chromatography (SEC).

According to the result of SDS-PAGE analysis shown in FIG. 3, only the soluble expression of MBP-CRM197 (103 kD) and the first purification step by MBP affinity chromatography did not result in the optimum purity, and thus, the fusion partner MBP and CRM197 were separated by TEV enzyme, and CRM197 of the cleaved proteins was purified using the C-terminal his-tag. The result is shown in FIG. 4. The specific purification method is as follows.

First, the cells were suspended in 20 mM Tris-HCl buffer (pH 7.4). Then, the cells containing the expressed protein were disrupted using an ultrasonicator and centrifuged at 13,000 rpm for 15 minutes to obtain the supernatant containing the soluble protein (FIG. 4, lane 1). For MBP purification, washing buffer A (20 mM Tris-HCl pH 7.4, 200 mM NaCl, mM EDTA) and elution buffer B (20 mM Tris-HCl pH 7.4, 200 mM NaCl, mM EDTA, 10 mM maltose) were used, and separation was carried out using a concentration gradient of elution buffer B at a flow rate of 1 ml/min (FIG. 4, lane 2).

In order to separate MBP, the MBP-CRM197 fraction recovered from the MBP purification was treated with 1 μl of TEV enzyme (SIGMA, 20 U) per 10 μg of the protein at 20° C. for 14 hours (FIG. 4, lane 3). As shown in FIG. 4, the separated proteins and TEV could be found.

Then, only the cleaved CRM197 was purified by His-tag affinity chromatography (IMAC) after buffer exchange for the reaction solution through ultrafiltration (UF) (FIG. 4, lane 4). His-tag affinity chromatography was performed with washing buffer A (20 mM sodium phosphate buffer pH 7.4, 500 mM NaCl) and elution buffer B (20 mM sodium phosphate buffer pH 7.4, 500 mM NaCl, 250 mM imidazole) at a flow rate of 1 ml/min.

Then, the active fractions obtained by His-tag affinity chromatography were separated by size-exclusion chromatography (SEC) for high purity purification (FIG. 4, lane 5). SEC was performed by flowing the buffer (20 mM potassium phosphate pH 6.0, 200 mM NaCl) at a flow rate of 1 ml/min to separate the fractions according to the molecular weight.

The final yield was calculated from each purification step from 1 L of the culture solution according to the above-mentioned specific method, and the result is shown in Table 1 below. The final yield of the finally expressed CRM197 protein was found to be 28.9% when it was calculated after excluding the molecular weight of the fusion partner MBP from that of the initial protein.

In addition, the result of culturing with 3 L of the culture solution in a 5-L jar and purification is shown in Table 2 below. Due to improvement in the environmental condition, cell growth and production were improved. Specifically, a medium supplemented with 20 g/l of yeast extract and 0.01 to 0.1 mg/l of trace elements (Zn, Fe, Co and Cu), based on the LB medium used for the flask culture, was used. The amount of air current was adjusted to 1 vessel volumes per minute (vvm) at 34° C., and the cells were cultured for 4 hours at 240 rpm after inoculation of 10% seed culture solution and for 24 hours at 500 rpm after induction with 0.1 mM IPTG. Under this culture condition, the production amount was increased to 3 g/l or more, and the cells obtained from the final culture solution was purified according to the above-mentioned purification process.

TABLE 1

| Step | Vol (mL) | Conc. for fusion (g/l) | Conc. for crm (g/l) | Total crm (mg) | Yield* Total | Yield* Step |
|---|---|---|---|---|---|---|
| Culture (OD 20) | 1000 | 0.33 | 0.19** | 187.4 | 100.0% | — |
| MBP | 100 | 1.82 | 1.03 | 103.3 | 55.1% | 55.1% |
| Bfr. Exchange | 50 | 3.09 | 1.76 | 87.8 | 46.8% | 85.0% |
| TEV treatment | 50 | — | 1.74 | 86.9 | 46.4% | 99.0% |
| Ni-NTA | 30 | — | 2.46 | 73.8 | 39.4% | 84.9% |
| Bfr. Exchange | 30 | — | 1.98 | 59.4 | 31.7% | 80.5% |
| SEC(Superdex 875) | 50 | — | 1.08 | 54.2 | 28.9% | 91.2% |

*Yield was calculated with crm in the absence in MBP
**mol. Fraction = 0.568

TABLE 2

| Step | Vol (mL) | Conc. for fusion (g/l) | Conc. for crm (g/l) | Total crm (g) | Yield* Total | Yield* Step |
|---|---|---|---|---|---|---|
| Culture (OD 60) | 3000 | 3.12 | 1.77** | 5.32 | 100.0% | — |
| MEP | 300 | 16.88 | 9.59 | 2.88 | 54.1% | 54.1% |
| Bfr. Exchange | 150 | 28.36 | 16.11 | 2.42 | 45.4% | 84.0% |
| TEV treatment | 150 | — | 15.82 | 2.37 | 46.4% | 98.2% |
| Ni-NTA | 90 | — | 22.43 | 2.02 | 38.0% | 85.1% |
| Bfr. Exchance | 90 | — | 18.01 | 1.62 | 30.5% | 80.3% |
| SEC(Superdex 575) | 150 | — | 9.86 | 1.48 | 27.8% | 91.2% |

*Yield was calculated with crm in the absence in MBP
**mol. Fraction = 0.568

Example 4: SEC Analysis of Purified CRM197

Finally, the isolated and purified CRM197 was analyzed by size exclusion HPLC (TOSOH, TSKgel-G3000Swx1) method. For SEC chromatographic analysis, the isolated and purified CRM197 was developed using washing and elution buffer (20 mM potassium phosphate pH 6.0, 200 mM NaCl) at a flow rate of 1 ml/min and detection was performed at 220 nm wavelength. The result is shown in FIG. 5.

Also in the SEC chromatogram result, CRM197 was found at a molecular weight of 61 kD. As shown in FIG. 5, no other protein peak was noted.

Example 5: Determination of Antigenicity and Immunogenicity of CRM197

Figure 6:
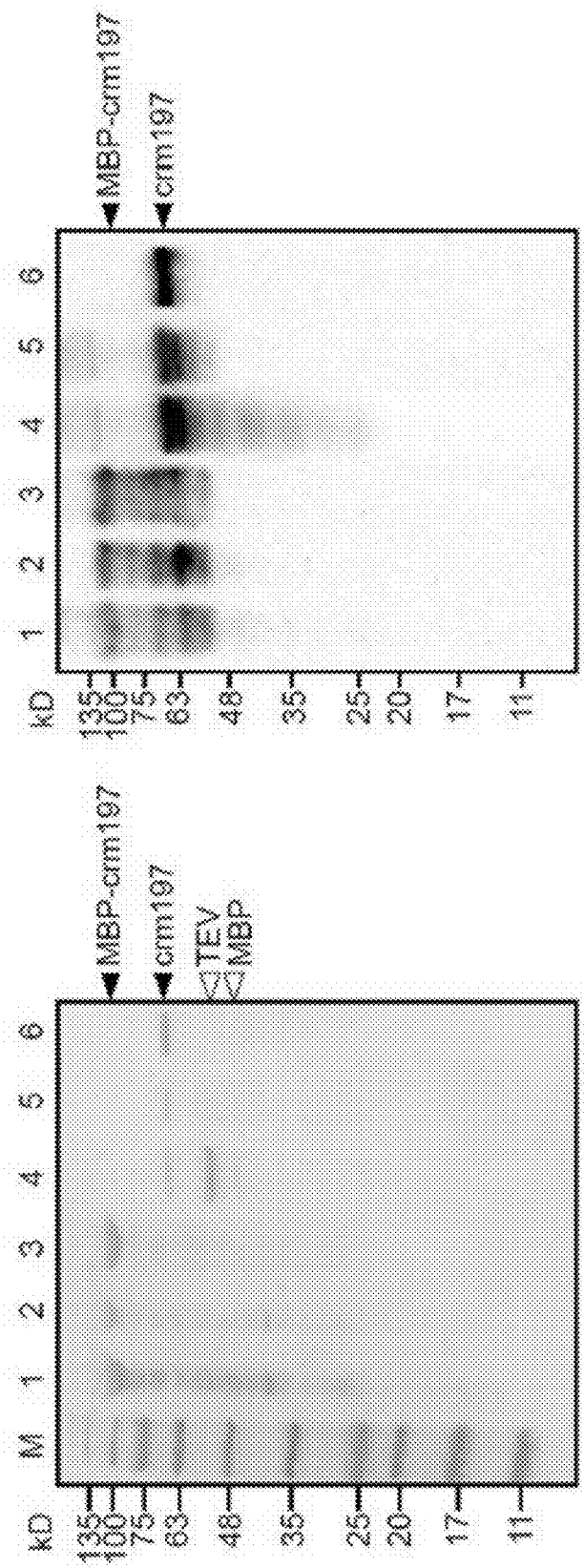
FIG. 6 is photographs showing the result of Western blot using anti-diphtheria toxin (DT) of each sample obtained in each purification step in Example 5 of the present invention.

In order to determine the antigenicity and immunogenicity, Western blot using anti-diphtheria toxin (DT) of each sample obtained in each purification step was performed, and the result is shown in FIG. 6.

Each sample obtained in each purification step was developed by SDS-PAGE (FIG. 6(*a*)). Then, the protein was adsorbed onto Immuno-blot poly-vinyl difluoride (PVDF) membrane using an instrument (semi-dry transfer, Biorad), and the analysis was achieved by Western blot method with mouse monoclonal anti-diphtheria toxin as primary antibody and goat polyclonal anti-mouse-IgG-HRP as secondary antibody (FIG. 5(*b*)). In Lanes 1 to 3, the weak signals (WB signals) are considered to be due to the reduction in membrane transfer efficiency above 100 kD. An unspecific band was noted in the unpurified sample, but the binding with CRM197 was clearly noted as the purity of the sample increased.

Example 6: Determination of Antigen Specificity of CRM197

In addition to the Western blot analysis, in order to determine the antigen specificity of CRM197, ELISA was performed with mouse monoclonal anti-diphtheria toxin and non-specific MBP-GCN4 protein as a control in a purified CRM197-attached 96-well plate. The result is shown in FIG. 7.

Specifically, CRM197 was attached to a 96-well plate for 1 hour and then the plate was washed with PBS-BSA (0.5%) solution to remove the excess unattached protein. Mouse monoclonal anti-diphtheria toxin as primary antibody and goat polyclonal anti-mouse-IgG-HRP as secondary antibody were attached to the plate. Reaction with O-phenylenediamine (OPD) as a substrate for detection was performed for 10 minutes at room temperature, and then 4.5N $H_2SO_4$ was added to terminate the reaction, and absorbance for this 96-well plate was measured at UV 490 nm wavelength.

Figure 7:
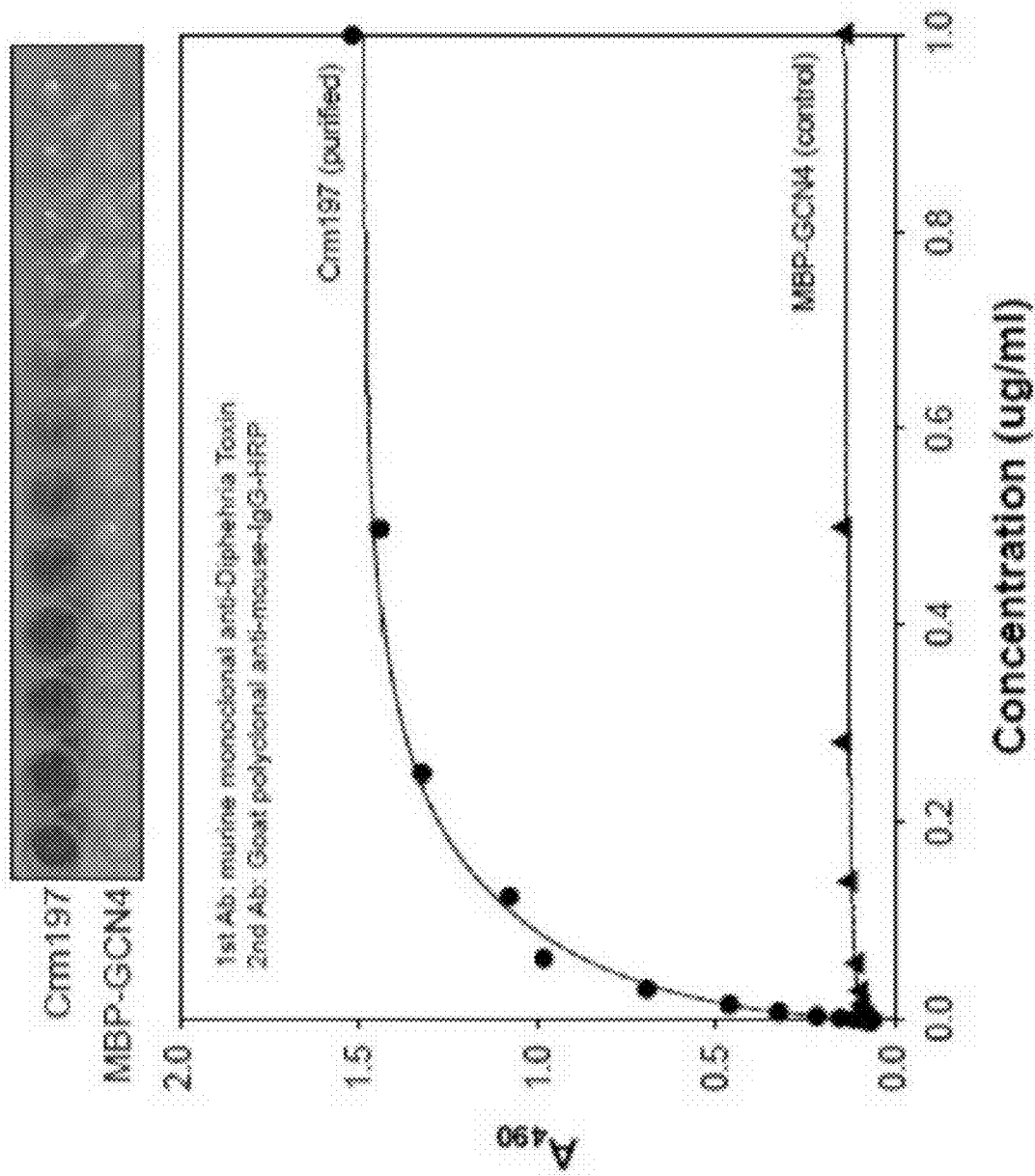
FIG. 7 is a photograph and a graph showing the result of ELISA analysis using anti-diphtheria toxin (DT) of the purified CRM197 in Example 6 of the present invention.

As shown in FIG. 7, the purified CRM197 was found to bind specifically to mouse monoclonal anti-diphtheria toxin, and no antigen specificity was observed in the control, MBP-GCN4. In particular, MBP-GCN4, which was used as a control, contains the fusion partner MBP, and thus, it is not likely to be detected as a false positive signal due to MBP also in the analysis of MBP-CRM197, which is the expression form.

Example 7: Determination of Folding of Purified Protein

It is known from Mitamura et al. (J. Biol. Chem. 1995, 270, 1015-9) that CRM197 binds to human heparin-binding epidermal growth factor-like growth factor (HB-EGF) in the correct structural state. Accordingly, in order to determine whether the folding of the purified protein was made correctly, the binding affinity of the purified protein to HB-EGF was measured by an ELISA method according to the method for investigating correct folding of CRM protein, specified in U.S. Patent Publication No. 2006/333057 and presented as standard test method of FDA. Specifically, according to the standard test method, HB-EGF prepared with varying concentration was bound to a 96-well plate to which the purified CRM197 was attached. For detection, rabbit monoclonal anti-HB-EGF antibody as primary antibody and anti-rabbit polyclonal IgG-HRP as secondary antibody were used for a sandwich ELISA method. The result is shown in FIG. 8.

Figure 8:
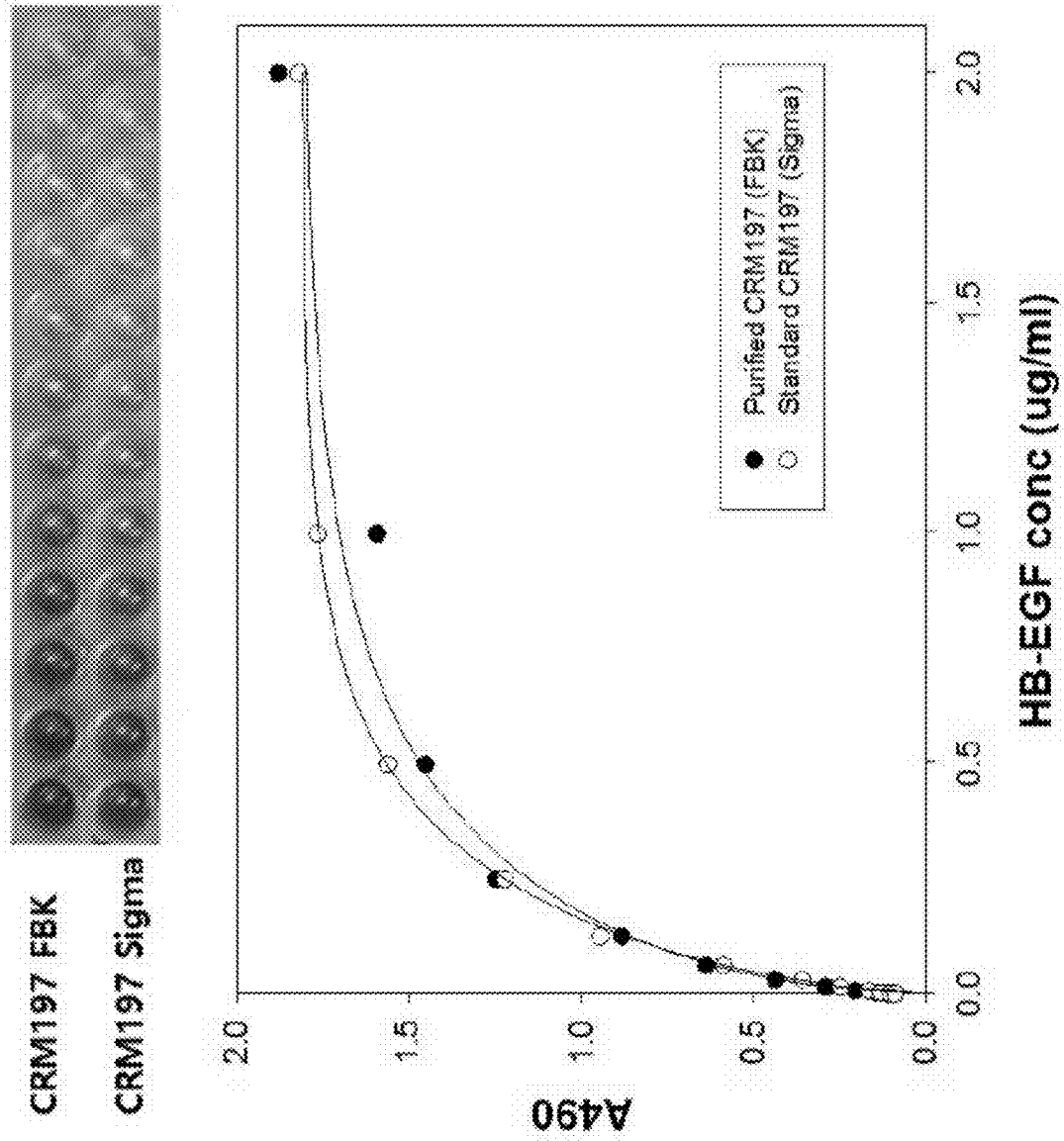
FIG. 8 is a photograph and a graph showing the result of measuring the HB-EGF binding affinity using ELISA in Example 7 of the present invention.

Referring to FIG. 8, correct folding can be determined by allowing HB-EGF in a concentration range of 0 to 2.0 µg/ml to bind to a 96-well plate to which the purified CRM197 and the standard (D2189, Sigma's CRM197) were attached, and detecting the amount of binding with the primary antibody and the secondary antibody. Accordingly, it is considered that the CRM197 obtained by purifying by multi-step chromatography the soluble protein expressed in *E. coli*, as described earlier, is folded into the correct structure and exhibits the antigenicity and immunogenicity equivalent to the native protein.

While the preferred embodiments of the present invention have been disclosed to solve the technical problem, those skilled in the art will appreciate that various modifications, changes, additions, etc. are possible, and such modifications, changes, etc. are to be considered as falling within the scope of the following claims.

The invention claimed is:

1. A method for producing a recombinant CRM197 protein soluble in cytoplasm, the method comprising a step of culturing recombinant *E. coli* harboring an expression plasmid carrying a gene sequence coding for a recombinant CRM197 protein under a condition suitable for expression of the recombinant CRM197 protein which has a histidine-tag attached to the C-terminus of CRM197 and a maltose-binding protein (MBP) attached to the N-terminus of CRM197, wherein a gene coding for the maltose-binding protein (MBP) is inserted into the N-terminus of the CRM197 using Nde I restriction enzyme, and a gene containing a Tobacco Etch Virus (TEV) protease cleavage site is inserted between the gene coding for the CRM197 and the gene coding for the maltose-binding protein (MBP) using BamH I restriction enzyme.

2. The method of claim 1, wherein the *E. coli* is endotoxin-free *E. coli* BL21 (DE3).

3. The method of claim 1, wherein the recombinant *E. coli* is BC-mC1h (Accession number: KCCM11958P).

4. The method of claim 1, further comprising a step of purifying after the culturing, wherein the step of purifying comprises a step of treating with tobacco etch virus (TEV) protease to remove the maltose-binding protein and a step of purifying the histidine tagged CRM197 via histidine-tag affinity chromatography.

* * * * *